US011676711B2

(12) United States Patent
Loerracher

(10) Patent No.: US 11,676,711 B2
(45) Date of Patent: Jun. 13, 2023

(54) METHOD FOR OPERATING A SYSTEM AND A SYSTEM

(71) Applicant: Roche Diabetes Care, Inc., Indianapolis, IN (US)

(72) Inventor: Tobias Loerracher, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 357 days.

(21) Appl. No.: 15/767,250

(22) PCT Filed: Oct. 13, 2016

(86) PCT No.: PCT/EP2016/074538
§ 371 (c)(1),
(2) Date: Apr. 10, 2018

(87) PCT Pub. No.: WO2017/064161
PCT Pub. Date: Apr. 20, 2017

(65) Prior Publication Data
US 2019/0088363 A1 Mar. 21, 2019

(30) Foreign Application Priority Data
Oct. 16, 2015 (EP) .................................... 15190162

(51) Int. Cl.
G16H 40/63 (2018.01)
A61B 5/00 (2006.01)
(Continued)

(52) U.S. Cl.
CPC ........... *G16H 40/63* (2018.01); *A61B 5/0002* (2013.01); *A61B 5/14532* (2013.01);
(Continued)

(58) Field of Classification Search
CPC ........ G16H 40/63; G16H 40/67; G16H 20/17; G16H 20/00; G16H 20/10; A61B 5/7475;
(Continued)

(56) References Cited

U.S. PATENT DOCUMENTS 8,126,733 B2 * 2/2012 Dicks ....................... A61N 1/08
705/2
8,428,722 B2 4/2013 Verhoef et al.
(Continued)

FOREIGN PATENT DOCUMENTS

CN 103002456 3/2013
CN 104657927 5/2015
(Continued)

OTHER PUBLICATIONS

Search Report for related CN201680060493.5 dated Jun. 2, 2020.

*Primary Examiner* — Robert A Sorey
*Assistant Examiner* — Kimberly A. Sass
(74) *Attorney, Agent, or Firm* — Woodard, Emhardt, Henry, Reeves & Wagner, LLP

(57) ABSTRACT

The present disclosure refers to a method for operating a system, the system comprising a medical device (1), having at least one of a sensor device for sensing medical data and a medication delivery device for delivering medication, a portable electronic consumer device (2), an intermediate device (3) provided with a first communication protocol for data communication with the portable electronic consumer device (2) and a second communication protocol for data communication with the medical device (1), and a control module (6) provided in the intermediate device (3), the method comprising, in the control module (6), receiving control data from the portable electronic consumer device (2) by a receiving functionality provided in the control module (6), the control data being configured for controlling operation of the medical device (1), determining whether the (Continued)

Figure 1:
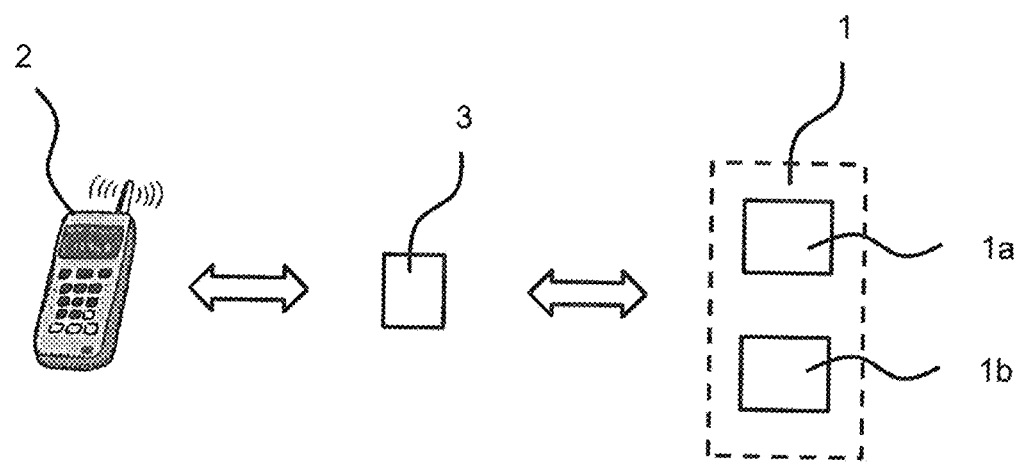

control data can be confirmed by a confirmation functionality provided in the control module (6), and if the control data are confirmed, transmitting the control data to the medical device (1) by a transmission functionality provided in the control module (6). Further, a system is provided.

10 Claims, 2 Drawing Sheets

(51) Int. Cl.
*A61B 5/145* (2006.01)
*G16H 20/17* (2018.01)
*G16H 40/67* (2018.01)
*G16H 20/10* (2018.01)

(52) U.S. Cl.
CPC .......... *A61B 5/4839* (2013.01); *A61B 5/6802* (2013.01); *A61B 5/7475* (2013.01); *G16H 20/10* (2018.01); *G16H 20/17* (2018.01); *G16H 40/67* (2018.01); *A61B 2560/0223* (2013.01); *A61B 2560/0271* (2013.01); *A61B 2560/0443* (2013.01); *Y02A 90/10* (2018.01)

(58) Field of Classification Search
CPC . A61B 5/6802; A61B 5/4839; A61B 5/14532; A61B 5/0002; A61B 2560/0271; A61B 2560/0223; A61B 2560/0443; Y02A 90/26; Y02A 90/22; Y02A 90/10

USPC .......................................................... 705/2
See application file for complete search history.

(56) References Cited

U.S. PATENT DOCUMENTS

| 2002/0002326 | A1 | 1/2002 | Causey et al. |
| 2007/0258395 | A1 | 11/2007 | Jollota et al. |
| 2010/0057057 | A1* | 3/2010 | Hayter ................ A61M 5/1723 604/890.1 |
| 2010/0162090 | A1 | 6/2010 | Emde et al. |
| 2010/0191086 | A1 | 7/2010 | Talbot et al. |
| 2010/0249887 | A1 | 9/2010 | Verhoef et al. |
| 2011/0264034 | A1* | 10/2011 | Roberts ............... G06F 19/3418 604/65 |
| 2011/0289497 | A1 | 11/2011 | Kiaie et al. |
| 2011/0320130 | A1* | 12/2011 | Valdes .................. G01D 18/00 702/19 |
| 2012/0232520 | A1* | 9/2012 | Sloan ...................... G16Z 99/00 604/504 |
| 2014/0128804 | A1 | 5/2014 | Strickland et al. |
| 2015/0182695 | A1 | 7/2015 | Rosinko |

FOREIGN PATENT DOCUMENTS

| CN | 104732468 | 6/2015 |
| EP | 2 386 971 A2 | 11/2011 |
| EP | 2 626 254 A1 | 8/2013 |
| WO | WO 2012/034255 A1 | 6/2012 |

* cited by examiner

METHOD FOR OPERATING A SYSTEM AND A SYSTEM

The present disclosure refers to a method for operating a system, and a system comprising a medical device and a portable electronic consumer device.

BACKGROUND

Document EP 2 656 254 A1 discloses a system with multiple medical devices. The system provides pass-thru data communication between an external computing device and each of the medical devices via a diabetes management device. A pass-thru module of the diabetes management device uses a set of pass-thru commands for establishing a pass-thru data communication path and enabling communication between the external computing device and the first medical device.

Document US 2002/0002326 A1 refers to a remote programmer for interfacing with at least one medical device. The medical device is one of art infusion device, a characteristic monitor, a characteristic meter, and an analyte sensor patch. The remote programmer is a personal data assistant (PDA). The medical device has a medical device module operatively coupled with the PDA via an interface. The PDA comprises a display being a touch screen element to interface with the medical device.

A system for sensing blood glucose data of a patient is disclosed in the document US 2010/0191086 A1. The system includes a sensor, a user interface, and an auxiliary device. The auxiliary device can be a patient monitor or other display or signal device, which displays information about the blood glucose data collected by the sensor.

Document U.S. Pat. No. 8,428,722 B2 discloses a communication device to facilitate communication between a medical device and a wireless communications network. The communication device comprises a telemetry circuit configured to wirelessly communicate with one or more medical devices, and a computer network communication interface configured to wirelessly communicate directly with a wireless computer network. The communication device also comprises a peripheral device communication interface configured to communicate with a wireless peripheral device and a processor being in operable communication with, and configured to control operations of, the telemetry circuit, the network communication interface, and the peripheral device communication interface.

A connector for use with a consumer electronic device and a medical device is disclosed in EP 2386 971 A2. The connector comprises a connecting structure for attaching the connector to the consumer electronic device, a first communication protocol for transmitting data between the medical device and the connector and a second communication protocol for transmitting data between the connector and the consumer electronic device. A software-based application is provided for receiving, managing and processing medical device data on a consumer electronic device, the software-based application comprising a graphical user interface for displaying data to a patient. The medical device is pre-programmed to communicate with the connector allowing communication between the consumer electronic device and the medical device through the connector, sending data from the medical device to the consumer electronic device via the connector, and processing and displaying the data on the connector or on the consumer electronic device.

Document US 2011/0289497 A1 refers to methods and systems for updating a medical device. Medical devices are configured for updates in response to various events including connection of a peripheral device to the medical device, a user initiated event, or based on received recommendations.

Document US 2010/0249887 A1 refers to a communications device for communication between a medical device and a wireless communications network, the device comprising a telemetry circuit configured to wirelessly communicate with one or more medical devices, and a computer network communication interface configured to wirelessly communicate directly with a wireless computer network. The communications device also comprises a peripheral device communication interface configured to communicate with a wireless peripheral device and a processor being in operable communication with, and configured to control operations of, the telemetry circuit, the network communication interface, and the peripheral device communication interface.

SUMMARY

It is an object of the present disclosure to provide a method for operating a system and a system comprising a medical device and a portable electronic consumer device which can be used in a greater variety of different use cases. Specifically, the safety of operation shall be improved with regard to operating the medical device.

According to aspects of the present disclosure, a method for operating a system and a system according to the independent claims 1 and 8, respectively, are provided. Embodiments are the subject of dependent claims.

According to one aspect, a method for operating a system is provided. The system comprises a portable electronic consumer device provided with a first communication protocol for data communication. The system further comprises a medical device, having at least one of a sensor device for sensing medical data and a medication delivery device for delivering medication, and a second communication protocol for data communication. There is an intermediate device provided with the first communication protocol for data communication with the portable electronic consumer device and the second communication protocol for data communication with the medical device. Also, with the system a control module is provided in the intermediate device. In the control module, the method comprises receiving critical control data from the portable electronic consumer device by a receiving functionality provided in the control module, the critical control data being configured for controlling a critical operation function of the medical device. The method further comprises determining whether the critical control data can be confirmed by a confirmation functionality provided in the control module. If the critical control data are confirmed, the method comprises transmitting the critical control data to the medical device by a transmission functionality provided in the control module, and operating the medical device according to the critical control data. The critical control data are configured to control at least one critical operation function of the medical device selected from the group: calibrating the sensor device, re-calibrating the sensor device, and delivering medication by the medication delivery device.

According to another aspect, a system is provided comprising a medical device, a portable electronic consumer device, an intermediate device, and a control module provided in the intermediate device. The medical device is having at least one of a sensor device for sensing medical data and a medication delivery device for delivering medication. The portable electronic consumer device is provided with a first communication protocol for data communication. The medical device is provided with a second communication protocol for data communication. The intermediate device is provided with the first communication protocol for data communication with the portable electronic consumer device and the second communication protocol for data transmission with the medical device. The control module is provided with a receiving functionality for receiving control data from the portable electronic consumer device, the control data being configured for controlling operation of the medical device, a confirmation functionality for determining whether the control data can be confirmed by a confirmation function provided in the control module, and a transmission functionality for transmitting the control data to the medical device by a transmission function provided in the control module, if the control data are confirmed. If the control data are confirmed, the method comprises transmitting the control data to the medical device by a transmission functionality provided in the control module, and operating the medical device according to the control data. The control data comprise critical control data configured to control at least one critical operation function of the medical device selected from the group of critical operation functions: calibrating the sensor device, re-calibrating the sensor device, and delivering medication by the medication delivery device.

The intermediate device may also be referred to as bridging device. Different from known technologies the intermediate device shall not be limited to pass-through data transmission between the medical device and the portable electronic consumer device. As an alternative, the intermediate may be configured to block pass-through data transmission for data transmission between the medical device and the transportable electronic consumer device. In an alternative embodiment, the intermediate device may be configured for pass through-data communication for data different from the control data, such pass-through data communication being free of at least the confirmation process.

The control data received in the intermediate device from the portable electronic consumer device will only be transmitted to the medical device if the process of confirmation handled by the confirmation functionality will confirm the control data. The control data may be confirmed without amending the control data received, thereby, providing the control data, after confirmation, to the medical device without amending such data in the intermediate device. As an alternative, the control data received from the portable electronic consumer device may be amended in line with parameters set in the intermediate device. Following, the amended control data may be confirmed and send from the intermediate device to the medical device. In the confirmation process it is determined that at least some of the control data received in the intermediate device are not within the data limits, such control data may be amended to be within the data limits. For example, a sensor current and/or a time of operation of the medication delivery device may be out of range, thereby, not being within the data limits set. As part of the confirmation process, such control data may be amended to be within the data limit provided in the intermediate device.

The portable electronic consumer device may be selected from the following group of portable electronic consumer devices: mobile phone, and tablet computer.

The first and second data communication protocol may be provided by one or more device components such as a transmitter and a receiver implemented, for example, by a transceiver, the device components configured to send and receive electronic data according to the first and/or second communication protocol. The device configuration may be provided by software and/or hardware device elements or modules. The communication protocol may allow for wireless and/or wired data communication.

The sensor device may be a subcutaneous sensor, for example, a subcutaneous sensor for continuously monitoring an analyte in a bodily fluid such as a blood glucose level for a patient. The medication delivery device may comprise an insulin pump configured to provide insulin for medication.

The medical device is configured to perform a plurality of operation functions. One or all operation functions may be controlled by a plurality control data. For example, the operation functions of the medical device may comprises at least one of the following: detecting measurement data by the sensor device, processing the measurement data, sending and/or receiving measurement data, calibrating the sensor device, and delivering medication by the medication delivery device.

Critical control data being a subset of the plurality control data which may be processed by the medical device for operation are configured to control one or more critical operation functions. The critical operation functions are a subset of the operation functions not including all operation functions of the plurality of operation functions.

The delivering of medication may comprise at least one of starting medication delivery, interrupting medication delivery, and stopping medication delivery by the medication delivery device. In the intermediate device electronic information may be provided defining critical operation functions of the medical device. For example, a list of critical operation functions may be stored in a memory device of the intermediate device. In the course of the confirmation process handled by the confirmation functionality it may be determined whether the critical control data received from the portable electronic consumer device refer to at least on of the critical operation functions in the intermediate device. If it is determined that the control data received do not refer to a critical operation function of the medical device, such control data may be passed through to the medical device without confirmation. In such case pass-through data transmission may be provided. Otherwise, the critical control data received have to pass the confirmation process.

The determining may further comprise confirming the critical control data in response to receiving a user confirmation in the control module through an input device of the intermediate device. Receiving the user confirmation may comprise outputting the critical control data received at least in part through a display of the intermediate device. User confirmation may be received by an input device provided with the intermediate device. For example, a touch sensitive display may be provided. As an alternative, the user may be informed about a successful confirmation process, but still user confirmation is requested for finalizing the confirmation functionality. Transmission of the critical control data to the medical device may only take place after such finalizing step.

The determining may further comprise confirming the critical control data in response to receiving, in the control module, confirmation from a confirmation algorithm running in the intermediate device. The confirmation algorithm may be implemented in the intermediate device by a software application receiving the critical control data received in the intermediate device as an input.

The method may further comprise providing the confirmation if it is determined by the confirmation algorithm that the critical control data are within control data limits provided in a memory device of the intermediate device.

The method may further comprise receiving safety control data from the portable electronic consumer device by the receiving functionality provided in the control module, the safety control data being configured for controlling a safety operation function of the medical device; determining whether the safety control data can be confirmed by the confirmation functionality provided in the control module; if the safety control data are confirmed, transmitting the safety control data to the medical device by the transmission functionality provided in the control module; and operating medical device according to the safety control data; wherein the safety control data are configured to control at least one of the safety operation functions of the medical device selected from the following group: stopping current medication delivery by the medication delivery device, and manually operating medication delivery by the medication delivery device.

Safety control data being a subset of the plurality control data which may be processed by the medical device for operation are configured to control one or more safety operation functions. The safety operation functions are a subset of the operation functions not including all operation functions of the plurality of operation functions. The safety operation functions are different from the subset of critical operation functions.

The aspects disclosed with regard to the critical control data may apply to the safety control data as mutatis mutandis.

The providing of safety control data which may comprise generating safety control data in the intermediate device may provide for limited control functionality with regard to the medical device in the intermediate device. If the medication delivery device is provided with an insulin pump, the safety control data may refer to operating the insulin pump for delivering a manual bolus.

The method may further comprise receiving operation status data form the medical device in the intermediate device, the operation status data being indicative of an operation status of the medical device in response to operating the medical device according to the control data. After receiving the confirmed critical/safety control data in the medical device it is operated according to the control data. In response to such operation, in the medical device the operation status data may be gathered or generated. The operation status data may be transmitted from the intermediate device to the portable electronic consumer device, for example, by pass-through data transmission. Specifically, such pass-through data transmission is free of amending the data received prior to transmission.

The intermediate device may be performing bi-directional transmission with the medical device and the portable electronic consumer device. The bi-directional transmission of data may include at least one of transmitting the control data, and the operation status data.

The intermediate device may be a plug-in device pluggable into a plug socket of the portable electronic consumer device.

Intermediate device may be configured to exchange electronic data with the portable electronic consumer device and the medical device by at least one of wireless data communication and wired data communication.

With regard to the system, the intermediate device may be a plug-in device pluggable into a plug socket of the portable electronic consumer device. In general, a hardware connection may be provided between the portable electronic consumer device and the intermediate device. As an alternative, for data communication the intermediate device and the portable electronic consumer device may not be linked physically, but by a wireless data communication link.

The intermediate device may be configured to exchange electronic data with the portable electronic consumer device and the medical device by at least one of wireless data communication and wired data communication.

The intermediate device may be provided in a wearable device, for example, a bracelet.

The medical device may be configured to block any operation control of the medical device by critical/safety control data which are tried to be sent directly from the portable electronic consumer device. Only critical/safety control data confirmed in the intermediate device before are to be accepted by the medical device for operation.

The intermediate device may be configured to automatically control an analyte level by determining a control signal for an infusion device based on monitored analyte values. In the case of glucose being the analyte, the intermediate device may be configured to artificially mimic a pancreas. An algorithm may be provided for implementing such artificial mimic, for example, in the control module. The algorithm may comprise a semi-closed loop algorithm which requires at least some user interactions, e.g. night time closed loop delivery or closed loop delivery with manual prandial bolus delivery, or a fully-closed loop algorithm, which fully automates measurement and infusion at all times. Such algorithms are known in the art as such and may for instance comprise a method based on fuzzy logic, a proportional-integral-derivative control, and/or model predictive control.

In alternative, a method for operating a system may be provided. The system comprises a portable electronic consumer device provided with a first communication protocol for data communication. The system further comprises a medical device, having at least one of a sensor device for sensing medical data and a medication delivery device for delivering medication, and a second communication protocol for data communication. There is an intermediate device provided with the first communication protocol for data communication with the portable electronic consumer device and the second communication protocol for data communication with the medical device. Also, with the system a control module is provided in the intermediate device. In the control module, the method comprises receiving safety control data from the portable electronic consumer device by a receiving functionality provided in the control module, the safety control data being configured for controlling a safety operation function of the medical device. The method further comprises determining whether the safety control data can be confirmed by a confirmation functionality provided in the control module. If the safety control data are confirmed, the method comprises transmitting the safety control data to the medical device by a transmission functionality provided in the control module, and operating the medical device according to the safety control data. The safety control data are configured to control at least one safety operation function of the medical device selected from the group: stopping current medication delivery by the medication delivery device, and manually operating medication delivery by the medication delivery device.

According to an alternative, a method for operating a system is provided. The system is comprising a medical device, having at least one of a sensor device for sensing medical data and a medication delivery device for delivering medication; a portable electronic consumer device; an intermediate device (3) provided with a first communication protocol for data communication with the portable electronic consumer device and a second communication protocol for data communication with the medical device; and a control module provided in the intermediate device. The the method is comprising, in the control module: receiving control data from the portable electronic consumer device by a receiving functionality provided in the control module, the control data being configured for controlling operation of the medical device; determining whether the control data can be confirmed by a confirmation functionality provided in the control module; and, if the control data are confirmed, transmitting the control data to the medical device by a transmission functionality provided in the control module.

The control data may be configured to control at least one critical operation function of the medical device selected from the group of critical operation functions: sensing medical data by the sensor device, calibrating the sensor device, re-calibrating the sensor device, and delivering medication by the medication delivery device. The determining may further comprise confirming the control data in response to receiving a user confirmation in the control module through an input device of the intermediate device. The determining may further comprise confirming the control data in response to receiving, in the control module, confirmation from a confirmation algorithm running in the intermediate device. The method may further comprise providing the confirmation if it is determined by the confirmation algorithm that the control data are within control data limits provided in a memory device of the intermediate device. Further, the method may comprise providing safety control data in the intermediate device and transmitting the safety control data to the medical device, the safety control data being configured to control a safety function of the medical device. The providing may further comprise providing the safety control data for at least one safety function of the medical device selected from the following group: stopping current medication delivery by the medication delivery device, manually operating medication delivery by the medication delivery device, and reading out present measurement data sensed by the sensor device. The method may further comprise receiving operation status data form the medical device in the intermediate device, the operation status data being indicative of an operation status of the medical device in response to operating the medical device according to the control data. Further, the method may comprise the intermediate device performing bi-directional data transmission with the medical device and the portable electronic consumer device.

According to a further alternative, a system may be provided, the system comprising: a medical device, having at least one of a sensor device for sensing medical data and a medication delivery device for delivering medication; a portable electronic consumer device; an intermediate device provided with a first communication protocol for data communication with the portable electronic consumer device and a second communication protocol for data communication with the medical device; and a control module provided in the intermediate device, the control module being provided with a receiving functionality for receiving control data from the portable electronic consumer device, the control data being configured for controlling operation of the medical device, a confirmation functionality for determining whether the control data can be confirmed by a confirmation function provided in the control module, and a transmission functionality for transmitting the control data to the medical device by a transmission function provided in the control module, if the control data are confirmed.

The intermediate device may be a plug-in device pluggable into a plug socket of the portable electronic consumer device. The intermediate device may be configured to exchange electronic data with the portable electronic consumer device and the medical device by at least one of wireless data communication and wired data communication. The intermediate device may be provided in a wearable device.

DESCRIPTION OF FURTHER EMBODIMENTS

Figure 2:
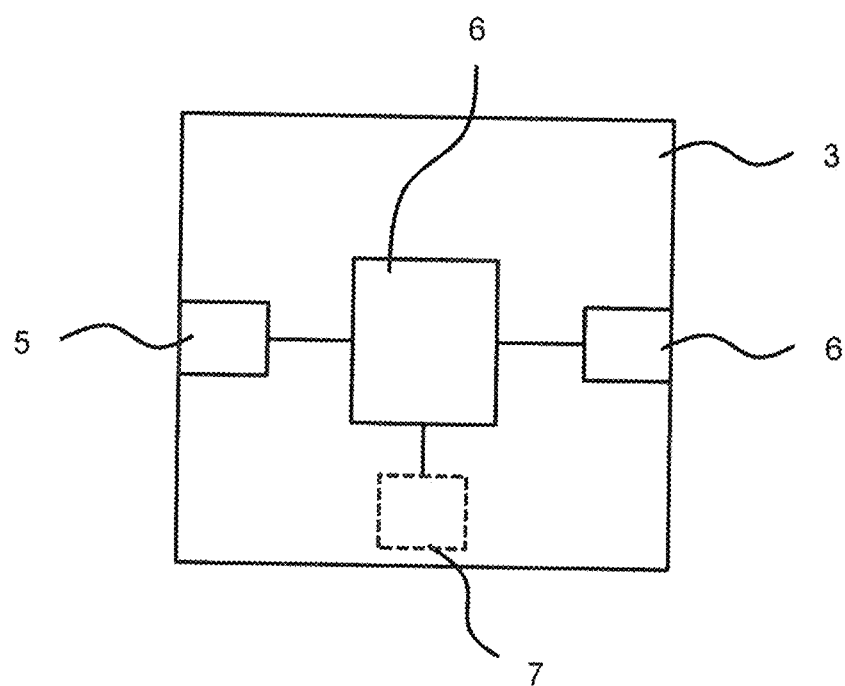

Following, further embodiments are described with reference to figures. In the figures, show:

FIG. 1 a schematic representation of a system comprising a medical device, an intermediate device, and a portable electronic consumer device;

FIG. 2 a schematic block diagram of the intermediate device; and

Figure 3:
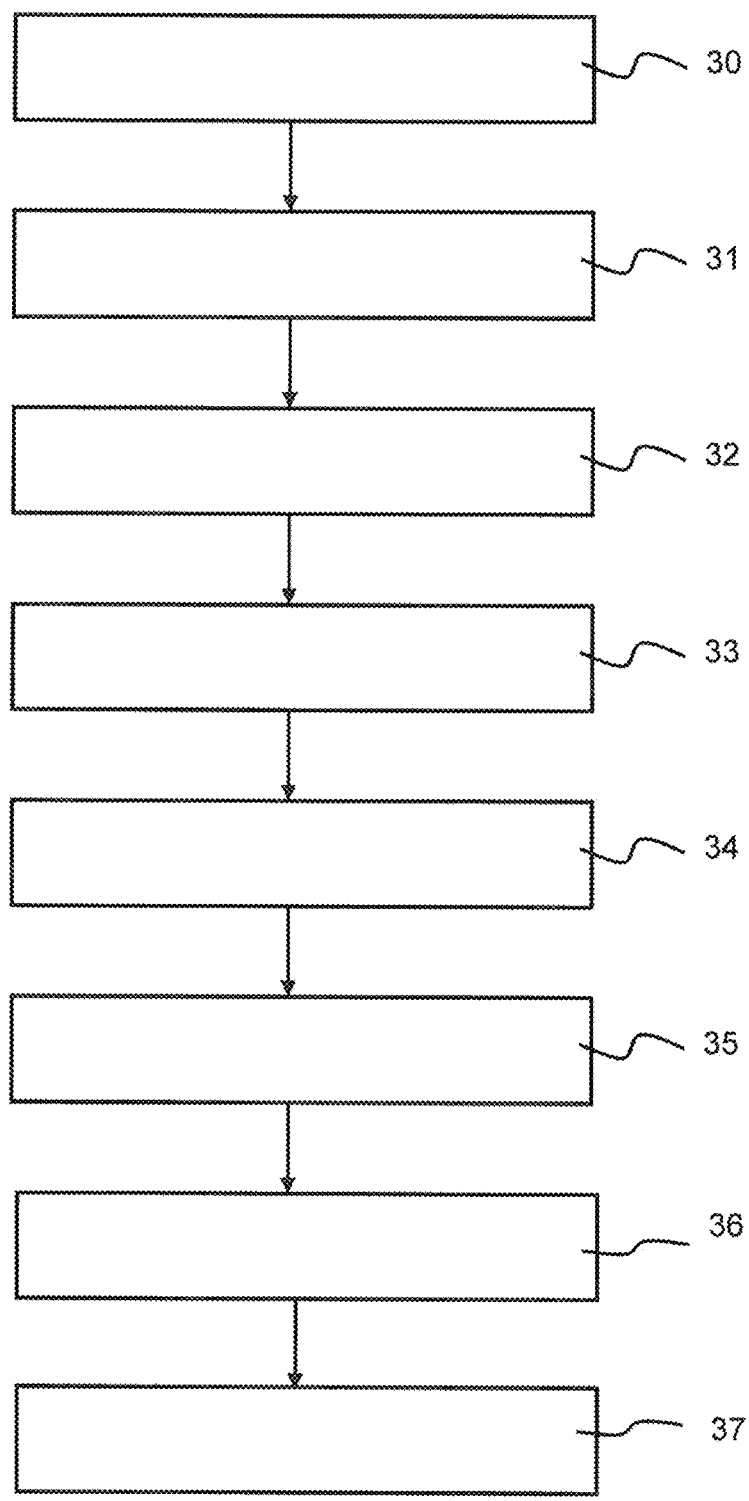

FIG. 3 a schematic block diagram of a method for operating the system.

FIG. 1 shows a schematic representation of a system comprising a medical device 1, a portable electronic consumer device 2, and an intermediate device 3 which may also be referred to as bridging device. The intermediate device 3 is provided with a first communication protocol for a data communication with the portable electronic consumer device 2 and a second communication protocol for the data communication with the medical device 1. The first and second data communication protocol may be the same. As an alternative, different communication protocols may be provided. Depending on the data communication standard necessary for data communication with the medical device 1 and the portable electronic consumer device 2, respectively, the intermediate device 3 is provided with the necessary communication protocol(s) for data communication.

The portable electronic consumer device 2 may be one of a mobile phone and a tablet computer.

The medical device 1 comprises at least one of a sensor device 1a for sensing medical data for a patient and a medication delivery device 1b for delivering medication. For example, medication for an infusion may be provided. The sensor device may be a subcutaneous sensor, for example, a subcutaneous sensor for continuously monitoring blood glucose level for a patient, such sensor being also referred to as subcutaneous CGM sensor. The medication delivery device may comprise an insulin pump configured to provide insulin for medication.

The portable electronic consumer device 2 is capable of receiving a user input. The user input may define control data for controlling operation of the medical device 1. For example, by the control data collecting medical data by the sensor device may be started. In addition or as an alternative, the control data provided in the portable electronic consumer device 2, specifically in response to the user input, may provide for controlling the medication delivery by the medication delivery device.

FIG. 2 shows a schematic representation of the intermediate device 3 comprising a data communication interface 4, a further data communication interface 5, and a control module connected to both the data communication interface 4 and the further data communication interface 5. A control module 6 connected to the data communication interfaces 4, 5 is provided with a processor for processing electronic data.

Also, a memory device 7 is provided, which, as an alternative, may be part of the control module 6.

The intermediate device 3 may exchange electronic data with the portable electronic consumer device 2 by wireless and/or wired data communication. The intermediate device 3 may be provided with a plug-in interface 7 to be plugged in a plug socket (not shown) of the portable electronic consumer device 2.

With the control module 6 a plurality of operation functionalities is provided in the intermediate device 3, for example, by one or more software applications running in the intermediate device 3. With regard to the operation functionalities, for further explanation it is referred to FIG. 3 which is a schematic block diagram of a method for operating the system shown in FIG. 1.

In a step 30, control data are provided in the portable electronic consumer device 2, for example, by receiving a user input for operation of the medical device 1. The control data are configured to control operation of the medical device 1, namely the sensor device for sensing medical data and/or the medical delivery device for delivering medication.

Different control data may be in the portable electronic consumer device 2. Critical control data may be provided, the critical control data being configured for controlling a critical operation function of the medical device 1. The critical control data are configured to control at least one critical operation function of the medical device 1 selected from the group: calibrating the sensor device, re-calibrating the sensor device, and delivering medication by the medication delivery device. In addition or as an alternative, safety control data may be provided, the safety control data being configured for controlling a safety operation function of the medical device 1. The safety control data are configured to control at least one of the safety operation functions of the medical device 1 selected from the following group: stopping current medication delivery by the medication delivery device, and manually operating medication delivery by the medication delivery device.

According to step 31, the control data are transmitted from the portable electronic consumer device 2 to the intermediate device 3. After receiving the control data in the intermediate device 3, by the control module 6, a confirmation process is performed in the intermediate device 3, the confirmation process being configured to confirm the control data received in the intermediate device 3. The confirmation process may be performed in step 32 for at least one of the critical control data and the safety control data, but not for other control data different from both the critical control data and the safety control data. Such other control data also provided in the intermediate device 3 may be provided through the intermediate device 3 to the medical device 1 without requiring confirmation. In general, the confirmation process may be performed for control data, but not for other control data different from the control data.

The confirmation process may comprise receiving user input through a user interface 8 of the intermediate device 3. For example, the user may provide input through a touch sensitive input device. As an alternative or in addition, the confirmation process being part of a confirmation functionality provided by the control module 6 may comprise running a confirmation algorithm in the control module 6.

In response to the confirmation process, the control data are confirmed, and the control data are transmitted from the intermediate device 3 to the medical device 1 (step 33). The control data, after confirmation, may be provided to the medical device 1 as received in the intermediate device 3 or as amended control data after being amended in the intermediate device 3.

Following, the medical device 1 is operated according to the received control data (step 34). In step 35, operation status data may be provided in the medical device 1. The operation status data are indicating a current operation status of the medical device 1 operated according to the control data. The apparatus status data, in step 36, are sent to the intermediate device 3. According to step 37, the operation status data are transmitted from the intermediate device 3 to the portable electronic consumer device 2 where the operation status data may be outputted, thereby, informing the user of the portable electronic consumer device 2 about operation status of the medical device 1.

The invention claimed is:

1. A method for operating a system comprising
   a portable electronic consumer device provided with a first communication protocol for data communication;
   a medical device, having at least one of a sensor device for sensing medical data and a medication delivery device for delivering medication, and provided with a second communication protocol for data communication;
   an intermediate device provided with the first communication protocol for data communication with the portable electronic consumer device and the second communication protocol for data communication with the medical device, the intermediate device including a memory device containing critical control data limits; and
   a control module provided in the intermediate device;
   the method comprising:
   the portable electronic consumer device transmitting critical control data to the control module;
   receiving in the control module the critical control data from the portable electronic consumer device by a receiving functionality provided in the control module, the critical control data being configured for controlling a critical operation function of the medical device;
   the control module determining that at least some of the critical control data are not within the data limits and in response the control module automatically amending such data to be amended critical control data within the data limits;
   in response to determining that at least some of the critical control data are not within the data limits, the control module transmitting the critical control data and the amended critical control data to the medical device, the transmitting being by a transmission functionality provided in the control module; and
   the control module operating the medical device according to the critical control data and the amended critical control data;
   wherein the critical control data and the amended critical control data are configured to control at least one of the critical operation functions of the medical device selected from the group consisting of: calibrating the sensor device, re-calibrating the sensor device, and delivering medication by the medication delivery device; and
   transmitting pass-through data different from the critical control data and the amended critical control data by the intermediate device in pass-through data communication, such transmitting pass-through data being free of at least the confirming.

2. The method according to claim 1, wherein the determining further comprises confirming the critical control data in response to receiving a user confirmation in the control module through an input device of the intermediate device.

3. The method according to claim 1, further comprising, in the control module,
receiving safety control data from the portable electronic consumer device by the receiving functionality provided in the control module, the safety control data being configured for controlling a safety operation function of the medical device;
confirming the safety control data by the confirmation functionality provided in the control module;
upon confirming the safety control data, transmitting the safety control data to the medical device by the transmission functionality provided in the control module; and
operating the medical device according to the safety control data;
wherein the safety control data are configured to control at least one of the safety operation functions of the medical device selected from the following group: stopping current medication delivery by the medication delivery device, and manually operating medication delivery by the medication delivery device.

4. The method according to claim 1, further comprising receiving operation status data from the medical device in the intermediate device, the operation status data being indicative of an operation status of the medical device in response to operating the medical device according to the critical control data or the safety control data.

5. The method according to claim 1, further comprising performing, by the intermediate device, bi-directional data transmission with the medical device and the portable electronic consumer device.

6. A system, comprising
a portable electronic consumer device provided with a first communication protocol for data communication;
a medical device, having at least one of a sensor device for sensing medical data and a medication delivery device for delivering medication, and provided with a second communication protocol for data communication;
an intermediate device provided with the first communication protocol for data communication with the portable electronic consumer device and the second communication protocol for data communication with the medical device, the intermediate device including a memory device containing critical control data limits; and
a control module provided in the intermediate device, the control module having
a receiving functionality for receiving critical control data from the portable electronic consumer device, the critical control data being configured for controlling a critical operation function of the medical device;
a confirmation functionality for determining whether the critical control data can be confirmed by a confirmation function provided in the control module; and
a transmission functionality for transmitting the critical control data to the medical device by a transmission function provided in the control module, if the critical control data are confirmed;
the portable electronic consumer device being configured to transmit critical control data to the control module;
the control module being configured to confirm whether the critical control data is within or not within the critical control data limits,
the intermediate device and the control module further being configured to transmit the critical control data to the medical device only if the control module has confirmed that the critical control data is within the critical control data limits and if the control module determines that at least some of the critical control data are not within the data limits, then in response the control module is configured to automatically amend by the control module the critical control data not within the data limits to be amended critical control data within the data limits and the control module further configured to operate the medical device according to the critical control data and the amended critical control data;
wherein
the critical control data are configured to control at least one of the critical operation functions of the medical device selected from the group consisting of: calibrating the sensor device, re-calibrating the sensor device, and delivering medication by the medication delivery device; and
the intermediate device is configured for transmitting pass-through data different from the critical control data, such transmitting of pass-through data communication being free of at least the confirming.

7. The system according to claim 6, wherein the intermediate device is a plug-in device pluggable into a plug socket of the portable electronic consumer device.

8. The system according to claim 6, wherein the intermediate device is configured to exchange electronic data with the portable electronic consumer device and the medical device by at least one of wireless data communication and wired data communication.

9. The system according to claim 6, wherein the intermediate device is provided in a wearable device.

10. The method of claim 1 in which the portable electronic consumer device is a mobile phone or a tablet computer, and the medical device is a subcutaneous sensor or an insulin pump.

* * * * *